(12) United States Patent
Bolla

(10) Patent No.: US 6,699,486 B1
(45) Date of Patent: Mar. 2, 2004

(54) TREATMENT OR PREVENTION OF PHOTOAGING AND SKIN CANCER

(75) Inventor: John D. Bolla, Palm Coast, FL (US)

(73) Assignee: Bolla Corporation, Palm Coast, FL (US)

(*) Notice: Subject to any disclaimer, the term of this patent is extended or adjusted under 35 U.S.C. 154(b) by 100 days.

(21) Appl. No.: 09/715,345

(22) Filed: Nov. 17, 2000

Related U.S. Application Data

(60) Provisional application No. 60/166,270, filed on Nov. 18, 1999.

(51) Int. Cl.[7] .................................................. A61K 7/00
(52) U.S. Cl. ....................... 424/401; 514/568; 514/569; 514/570; 514/596; 514/629
(58) Field of Search ........................... 424/401; 514/596, 514/570, 568, 629, 569

(56) References Cited

U.S. PATENT DOCUMENTS

| | | |
|---|---|---|
| 5,409,899 A | 4/1995 | Fauchere et al. |
| 5,416,191 A | 5/1995 | Cheronis et al. |
| 5,563,162 A | 10/1996 | Oku et al. |
| 5,574,042 A | 11/1996 | Oku et al. |
| 5,597,803 A | 1/1997 | Breipohl et al. |
| 5,610,140 A | 3/1997 | Goodfellow et al. |
| 5,620,958 A | 4/1997 | Cheronis et al. |
| 5,635,593 A | 6/1997 | Cheronis et al. |
| 5,700,779 A | 12/1997 | Goodfellow et al. |
| 5,750,506 A | 5/1998 | Goodfellow et al. |
| 5,750,699 A | 5/1998 | Oku et al. |
| 5,834,431 A | 11/1998 | Stewart et al. |
| 5,843,900 A | 12/1998 | Cheronis et al. |
| 5,849,312 A * | 12/1998 | Breton et al. ............... 424/401 |
| 5,849,863 A | 12/1998 | Stewart et al. |
| 5,863,899 A | 1/1999 | Cheronis et al. |
| 5,968,951 A | 10/1999 | Dodey et al. |
| 6,080,758 A | 6/2000 | Dodey et al. |

FOREIGN PATENT DOCUMENTS

| | | |
|---|---|---|
| EP | 0 596 406 A1 | 5/1994 |
| EP | 0 622 361 A1 | 11/1994 |
| EP | 0 596 406 B1 | 12/1998 |
| WO | WO 96/13485 | 5/1996 |
| WO | WO 96/40639 | 12/1996 |
| WO | WO 97/07115 | 2/1997 |
| WO | WO 97/11069 | 3/1997 |

OTHER PUBLICATIONS

Bhoola et al., "Bioregulation of Kinins: Kallikreins, Kininogens, and Kininases," *Pharmacological Reviews*, 44:1–80 (1992).

Fisher et al., "Cellular, Immunologic and Biochemical Characterization of Topical Retinoic Acid–Treated Human Skin," *J. Invest. Dermatol.*, 96:699–707, (1991).

Fisher et al., "Molecular Basis of Sun–induced Premature Skin Aging and Retinoid Antagonism," *Nature*, 379:335–339, (1996).

Fisher et al., Pathophysiology of Premature Skin Aging Induced By Ultraviolet Light, *N. Engl. J. Med.*, 337:1419–1428, (1997).

Regoli et al., "Pharmacology of Bradykinin and Related Kinins," *Pharmacological Reviews*, 32:1–46 (1980).

* cited by examiner

*Primary Examiner*—Shelley A. Dodson
(74) *Attorney, Agent, or Firm*—Clark & Elbing LLP; Kristina Bieker-Brady

(57) ABSTRACT

Disclosed herein are methods for the treatment or prevention of photoaging or skin cancer in a patient. These methods include administering a compound that inhibits a component of the kallikrein inflammatory pathway in an amount sufficient to reduce one or more symptoms of photoaging or skin cancer.

26 Claims, 1 Drawing Sheet

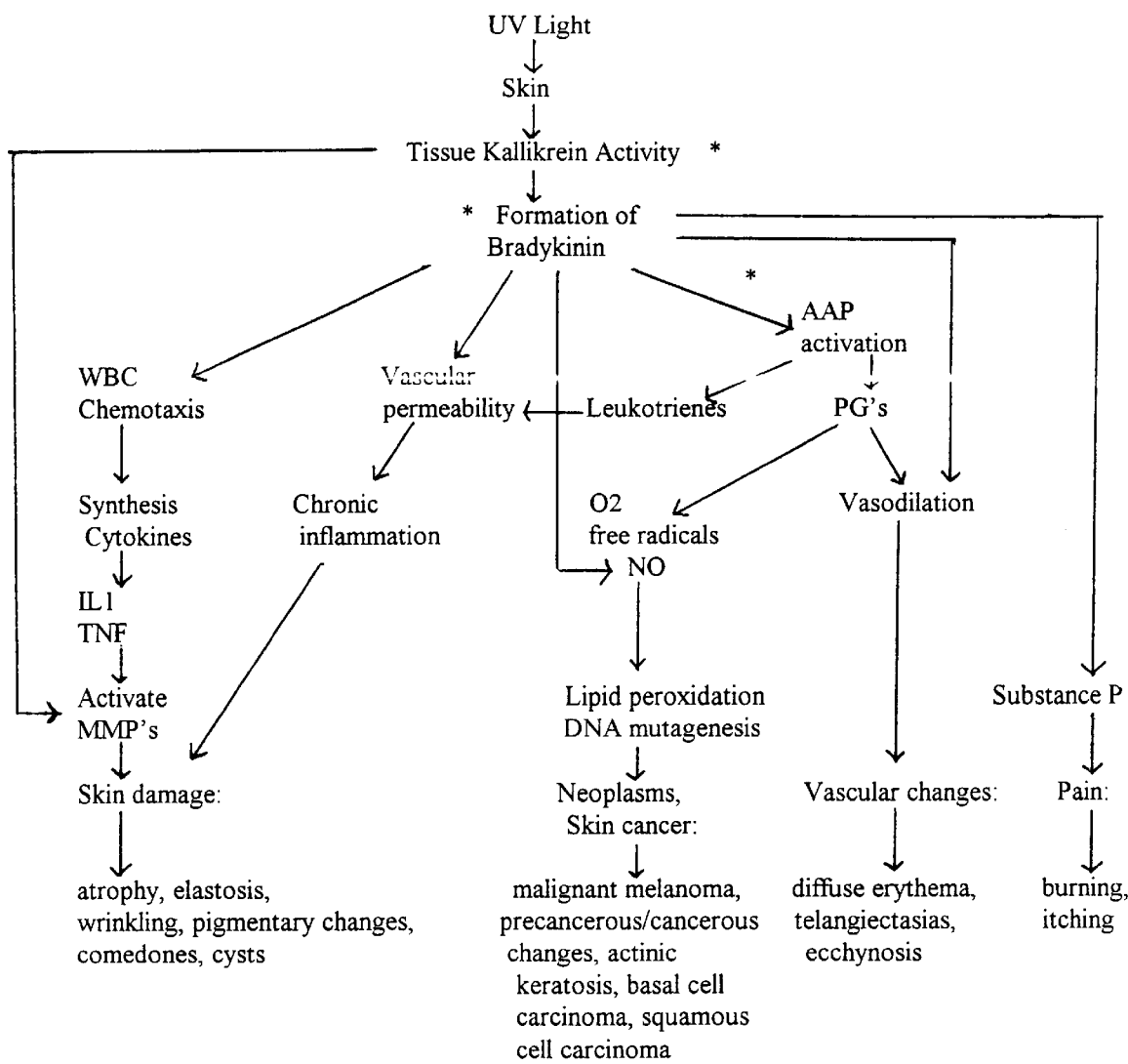
Fig. 1    PATHWAY OF PHOTOAGING

TREATMENT OR PREVENTION OF PHOTOAGING AND SKIN CANCER

CROSS REFERENCE TO RELATED APPLICATIONS

This application claims priority from United States provisional application U.S. Ser. No. 60/166,270, filed Nov. 18, 1999.

BACKGROUND OF THE INVENTION

This invention relates to methods for treating or preventing the skin photoaging process and skin cancer.

Photoaging, or premature aging, is a process in which the skin changes in appearance as a result of repeated exposure to sunlight. Typically, photoaging occurs in areas of habitual exposure, such as the scalp, face, ears, neck, chest, forearms, and hands. The changes associated with photoaging include elastosis, atrophy, wrinkling, vascular changes (diffuse erythema, ecchymoses, and telangiectasias), pigmentary changes (lentigines, freckles, and areas of hypo- and hyperpigmentation), and the development of seborrheic keratosis, actinic keratosis, comedones, and cysts. By contrast, chronologically-based aging of sun-protected skin results in skin that has thinned and lost elasticity, but which has otherwise remained smooth and unblemished.

Exposure to sunlight causes DNA mutagenesis, enzyme inactivation, inhibition of cell division, and cell death, therefore increasing the risk of developing skin cancers including basal cell carcinomas, squamous cell carcinomas, and malignant melanomas. The principle mediator of the carcinogenesis in the skin involves the formation of pyrimidine dimers between thymidine-thymidine, cytosine-thymidine, and cytosine-cytosine nucleotide pairs.

The ultraviolet (UV) component of sunlight, especially the middle UV (called UVA/B, 290–400 nm wavelength), is thought to be the principal causative agent which induces the photoaging and carcinogenic effects of sunlight in skin. Oxygen free radicals, which increase upon UV exposure, have been proposed to be mediators of the photoaging and carcinogenic effects of UV light (Reiger, Cosmetics and Toiletries 108: 43–56, 1993; Southorn PA, Free radicals in medicine. 1. Chemical nature and biologic reactions. Mayo Clin. Proc. 63: 391, 1988). Free radicals are highly reactive molecules with unpaired electrons in the outer orbital. While free radicals perform some beneficial tasks, such as participating in the destruction of microorganisms and cancer cells, excessive levels can lead to DNA mutagenesis and damage to cellular structure (Southorn, supra).

Matrix metalloproteases (MMPs), which degrade collagens, elastins, and other proteins in the connective tissue network, are also proposed to be mediators of photoaging. Upon UV exposure, the transcription factors AP-1 and NF-κB are increased, which, in turn, increase expression of MMPs, such as collagenase, 92 kD gelatinase, and stromelysin-1 (Fisher et al., N. Engl. J. Med. 337: 1419–1428, 1997).

Based on the above proposed mechanisms, the use of antioxidants to reduce oxygen free radicals in the skin and the use of compounds that inhibit the components of the MMP pathway have been disclosed as treatments for UV-based skin cancer and photoaging (Southorn, supra; Fisher et al., N. Engl. J. Med. 337: 1419–1423, 1997; Voorhees et al., U.S. Pat. No. 5,837,224). Given that these treatments have resulted in only marginal success, there is a clear need for the identification of new targets in the photoaging and carcinogenic processes and the development of drugs that affect these new targets.

The kallikrein-kinin pathway includes kallikreins and bradykinins. Kallikreins are serine proteases, and are divided into two principal groups: tissue kallikreins (EC number 3.4.21.35) and plasma kallikrein (EC number 3.4.21.34).

Plasma kallikrein has a molecular weight of about 100 kD, circulates in the blood in a precursor form called prekallikrein, and is principally involved in the activation of the blood clotting and complement enzyme cascades.

Tissue kallikreins, otherwise known as glandular or organ kallikreins, are glycoproteins with a molecular weight ranging from 27–40 kD. They have been isolated from various tissue and body fluids including saliva, intestine, lung, brain, plasma, and the sweat glands of the skin. Their substrates include procollagenase, kininogen, proinsulin, prorenin, BAM 22P atrial natriuretic factor, low density lipoprotein, atriopeptigen, and tissue plasminogen activator.

The major effectors of kallikrein activation are bradykinin, Lys-bradykinin (kallidin), and Met-Lys bradykinin, which are produced by kallikrein cleavage of kininogen. Kininogen is a hepatic-derived protein which circulates in the blood in a low molecular weight form and a high molecular weight form. Tissue kallikreins are relatively specific for cleavage of the low molecular weight form; plasma kallikrein has greater specificity for the high molecular weight form.

Bradykinins are autocoids, that is, they are hormones that are synthesized locally and act locally. This local effect is due to the short half-life (less than 30 seconds) of bradykinins and their almost complete destruction in the first pass through the pulmonary circulation (Ferreira and Vane, Chemotherap. 30: 317, 1967). In addition to playing a role in inflammation, bradykinins also lower blood pressure, participate in blood clotting and complement reactions, mediate rhinitis, and cause pain.

The major effects induced by bradykinins are vasodilation, increased vascular permeability, and inflammation. The inflammatory process involves the infiltration of neutrophils, macrophages, lymphocytes, mast cells, and other lamina proprira cells, including fibroblasts, to the site of inflammation. These inflammatory cells then function to synthesize and release several arachidonic acid-related mediators of inflammation, such as prostaglandins, leukotrienes, and thromboxanes.

SUMMARY OF THE INVENTION

The invention features a method of treating or preventing photoaging of the skin. The method includes administering a compound to a patient that inhibits one or more components of the kallikrein-kinin pathway in an amount sufficient to reduce or prevent a symptom of photoaging. The symptom of photoaging is mediated by activation of the pathway, and can be caused by inflammation, vasodilation, or increased vascular permeability in the skin. Examples of symptoms of photoaging that can be reduced or prevented by the method of the invention include elastosis, atrophy, wrinkling, vascular changes, pigmentary changes, seborrheic keratosis, actinic keratosis, comedones, and cysts.

The compound can be administered systemically or topically. The compound can be in a liposomal formulation and is preferably administered immediately prior to, or during, photoexposure. Preferably, the compound is a nonsteroidal antiinflammatory drug (NSAID), or inhibits bradykinin activity, preferably, it inhibits bradykinin activation of the BK2 receptor, or inhibits kallikrein activity, more preferably, tissue kallikrein activity.

Another aspect of the invention features a method of assessing whether an inhibitor of the kallikrein-kinin pathway is an effective compound for treating or preventing photoaging. The method includes contacting the compound with skin before, during, or after photo or UV exposure, and measuring whether the compound significantly reduces a kallikrein-kinin pathway related change in the skin.

The invention also includes a method of treating or preventing skin cancer. The method includes administering a compound to a patient that inhibits one or more components of the kallikrein-kinin pathway in an amount sufficient to reduce or prevent a symptom of skin cancer. The symptom of skin cancer is mediated by activation of the pathway, and can be caused by inflammation, vasodilation, increased vascular permeability, and generation of nitric oxide and oxygen free radicals in the skin. Examples of symptoms of skin cancer that can be reduced or prevented by the method of the invention include precancerous or cancerous changes to skin morphology, actinic keratosis, basal cell carcinomas, squamous cell carcinomas, and malignant melanoma.

The compound can be administered systemically or topically, preferably, the compound is in a liposomal formulation and is administered immediately prior to, or during, photoexposure. Preferably, the compound is a non-steroidal anti-inflammatory drug (NSAID), or inhibits bradykinin activity, more preferably, the compound inhibits bradykinin activation of the BK2 receptor, or inhibits kallikrein activity, more preferably, tissue kallikrein activity.

Another aspect of the invention features a method of assessing whether an inhibitor of the kallikrein-kinin pathway is an effective compound for treating or preventing skin cancer. The method includes contacting the compound with skin before, during, or after photo or UV exposure, and measuring whether the compound significantly reduces a kallikrein-kinin pathway related change in the skin. The change in the skin can be increased oxygen free radicals or increased DNA mutagenesis.

By "a kallikrein" is meant a tissue kallikrein or plasma kallikrein.

By "a bradykinin" is meant bradykinin, Lys-bradykinin (kallidin), or Met-Lys bradykinin.

By "an enzyme in the arachidonic acid metabolic pathway" is meant an enzyme, such as cyclooxygenase, lipoxygenase, or prostaglandin synthetase, that plays a role in converting arachidonic acid to various products such as prostaglandins, leukotrienes, and thromboxanes.

By "a component of the kallikrein-kinin pathway" is meant a kallikrein, a bradykinin, or an enzyme in the arachidonic acid metabolic pathway that plays a role in the activation of the kallikrein-kinin pathway and causes the onset of a symptom of photoaging or skin cancer by mediating a kallikrein-kinin pathway-related change in the skin.

By "an inhibitor of the kallikrein-kinin pathway" is meant a compound that inhibits a component of the kallikrein-kinin pathway, such that the activation of the pathway, for example, following exposure to the sun, is reduced. This inhibition results in a reduced occurrence of a symptom of photoaging or skin cancer, or a reduction in a kallikrein-kinin pathway-related change in the skin, following activation of the pathway. The inhibitor either inhibits or antagonizes the enzymatic or hormonal activity of the component or reduces the protein level of the component.

By "a kallikrein-kinin pathway-related change in the skin" is meant a change mediated by the activation of the kallikrein-kinin pathway, for example, inflammation, infiltration of inflammatory cells, vasodilation, increased vascular permeability, increased oxygen free radicals, increased nitric oxide, increased DNA mutagenesis (for example, pyrimidine dimerization), increased matrix metalloproteases (MMPs), increased deposition of elastin material, reduced types I and III collagen precursors, or an increased ratio of type III to type I collagen.

By "a symptom of photoaging" is meant one of the following symptoms that occur in response to habitual exposure of the skin to sunlight: elastosis (an increased coarseness and yellowing discoloration of the skin); atrophy (thin and easily torn skin); wrinkling; vascular changes, for example, diffuse erythema, ecchymoses, and telangiectasias (dilation due to thinning of vessel walls); pigmentary changes, for example, lentigines (liver spots), freckles, and areas of hypo- and hyper-pigmentation; and the development of seborrheic keratosis, actinic keratosis, comedones (obstruction of ducts of the skin), and cysts.

By "a symptom of skin cancer" is meant one of the following symptoms that occur in response to habitual exposure of the skin to sunlight: the appearance of precancerous or cancerous changes to skin morphology, including actinic keratosis, basal cell carcinomas, squamous cell carcinomas, and malignant melanoma.

By "treating or preventing photoaging" or "treating or preventing skin cancer" is meant producing a detectable reduction in a symptom of photoaging or skin cancer, respectively, or preventing the occurrence or exacerbation of a symptom under conditions known to induce such symptoms, such as sun exposure.

By "a kallikrein inhibitor" is meant a compound which causes a reduction of kallikrein enzymatic activity or protein level and includes, but is not limited to, serpin, C1 inhibitor, $\alpha 2$ macroglobulin, antithrombin-III, ecotin, and broad spectrum Kunitz-type serine protease inhibitors (such as aprotinin and its variants), an antibody to a kallikrein, diisopropylfluorophosphate, pefablock (Interchim), and other exemplary inhibitors listed in U.S. Pat. Nos. 5,786,328, 5,770,568, or 5,464,820.

By "a bradykinin inhibitor" is meant a compound that reduces the activity or level of the autocoid. Preferred inhibitors are icatibant and CP0597 (Cortech). Other exemplary inhibitors include, but are not limited to, those listed in U.S. Pat. Nos. 5,700,779; 5,750,506; 5,610,140; 5,863,899, 5,849,863; 5,843,900; 5,834,431, 5,635,593; 5,416,191; 5,620,958; 5,563,162; 5,750,669; 5,574,042; 4,801,613, 5,578,601, 4,693,993, WO 96/13485; WO 96/40639; WO 97/07115; WO 97/11069; EP 773,932 A1; EP 596,406 A1; EP 596,406 B1; EP 787,131 A1; EP 861,243 A1; EP 807,105 A1; EP 622,361 A1; U.S. Pat. No. 5,849,312; U.S. Pat. No. 5,212,182; EP 578,521; EP 564,972; EP 548,825; EP 552,106; FR 2,686,343; WO 93/11789; and the indirect bradykinin inhibitors listed in U.S. Pat. No. 4,801,613. Preferred inhibitors are specific for the BK2 receptor, such as icatibant and CP0597.

By "an inhibitor of the arachidonic acid metabolic pathway" is meant a compound that reduces the activity or level of cyclooxygenase, lipoxygenase, prostaglandin synthetase, or another enzyme that plays a role in converting arachidonic acid to its various metabolic products. Examples of such inhibitors include, but are not limited to, nonsteroidal anti-inflammatory drugs, salicylates, and cyclooxygenase inhibitors.

By "a nonsteroidal anti-inflammatory drug (NSAID)" is meant a compound that reduces inflammation. Preferred NSAIDs include, but are not limited to, naproxen, nabumetone, diclofenac, sulindac, oxaprosin, diflunisal, bromfenac, aspirin, piroxicam, indomethacin, etodolac, ibuprofen, fenoprofen, flurbiprofen, ketorolac, nimesulide, NS-398, ketoprofen, trisalicylates, acetaminophen, oxaprosin, salsalate, rofecoxib, and celecoxib.

Other features and advantages of the invention will be apparent from the following detailed description, and from the claims.

BRIEF DESCRIPTION OF THE FIGURE

FIG. 1 is a diagram of the kallikrein-kinin pathway, which demonstrates the causal connection between sunlight- or UV light-induced activation of the kallikrein-kinin pathway in the skin and the onset of symptoms of photoaging and skin cancer. FIG. 1 also points out the components of the kallikrein-kinin pathway that are inhibited to treat or prevent symptoms of photoaging or skin cancer (see stars).

DETAILED DESCRIPTION

The present invention arises from my discovery of a causal connection between the local activation of the kallikrein-kinin pathway in the skin (caused by exposure to sunlight, for example) and the occurrence of symptoms of photoaging and skin cancer. Accordingly, the present invention features a method of treating or preventing a symptom of photoaging or skin cancer by administering to a patient a compound that inhibits a component of the kallikrein-kinin pathway such that the effect of sun-induced activation of the pathway is reduced.

The Kallikrein-kinin Pathway is a Novel Mediator of Photoaging and Skin Cancer: A Rationale for Treatment I have found that activation of the kallikrein-kinin pathway, which is induced by exposure to sunlight, mediates the photoaging process and the development of skin cancer by increasing inflammation, vasodilation, and vascular permeability in the skin at the site of exposure, as shown schematically in FIG. 1.

Without wishing to be bound by any particular theory, I believe that the activation of the kallikrein-kinin pathway is due, at least in part, to the UV component of sunlight. The UV effect may be enhanced by the local increases in skin temperature that typically accompany exposure to sunlight and cause an increase in kallikrein release and bradykinin production in the skin (see, e.g., Regoli et al., Pharmacological Reviews 32: 1980; Bhoola et al., Pharmacological Reviews 44: 1992).

In further elaboration of my discovered causal connection, the sun-induced increase in kallikrein activity in the skin increases the formation of bradykinins, resulting in vasodilation, increased vascular permeability, and inflammation in the skin. The inflammation is due to a cytokine-induced migration of inflammatory cells, including mast cells, basophils, monocytes, macrophages, and leukocytes, to the site. These cells, in turn, release oxygen free radicals, nitric oxide, and extracellular proteases at the site.

The increase in oxygen free radicals induces the following: DNA mutagenesis, which causes skin cancers; the disruption of the maturation of keratinocytes in the skin, which causes actinic keratosis, a symptom of photoaging as well as skin cancer; reactive changes in melanocytes, which result in the photoaging symptoms of hypo- and hyperpigmentation; and damage to the structure and function of skin cells and the extracellular connective tissue matrix of the skin, which causes the photoaging symptoms of skin atrophy and wrinkling.

Oxygen free radicals are normally located within the intracellular compartment of inflammatory cells and they mediate the bactericidal activity of cells. However, once these reactive species are released from the inflammatory cells into the extracellular space of the skin, they induce lipid peroxidation and oxidation of protein sulfhydryl groups, and cross the plasma membrane to induce DNA damage in skin cells. These effects cause damage and degeneration of both the cells of the skin as well as the extracellular connective tissue matrix, resulting in DNA mutagenesis (skin cancer), changes in pigmentation (photoaging), and atrophy and wrinkling (photoaging). Nitric oxide released from the inflammatory cells has similar damaging effects on skin tissue.

Symptoms of photoaging that are related to damage to the skin's connective tissue matrix, such as atrophy and wrinkling, are also caused by the infiltration of inflammatory cells at the site of exposure and their release of extracellular proteases, such as procollagenase, elastase, and cathepsin G. Once activated (for example, procollagenase is cleaved to form the active collagenase), these proteases degrade the connective tissue network, especially when their presence is not counterbalanced by antiproteases, such as the tissue inhibitors of metalloproteinases (TIMPs). The effect of procollagenase released by kallikrein-kinin pathway activation is potentiated by the concurrent activation of kallikreins, because kallikreins recognize procollagenase as a substrate and convert it to collagenase.

In addition to the above-discussed DNA mutagenesis, changes in pigmentation, skin wrinkling, and skin atrophy, the sun-induced activation of the kallikrein-kinin pathway also causes other symptoms of photoaging via inflammation, vasodilation, or increased vascular permeability. For example, the repetitive sun-induced activation of the kallikrein-kinin pathway causes vascular abnormalities in the skin, such as the formation of diffuse erythema, telangiectasia, and ecchymosis. In addition, the chronic inflammation that results from repetitive kallikrein activation causes increased skin coarseness (elastosis) due to the abnormal deposition of elastin material that changes the functional properties of the connective tissue matrix.

In summary, the treatment of the present invention is based on my development, elaborated herein, of the causal relationship between the local, sun-induced activation of the kallikrein-kinin pathway and the development of symptoms of photoaging and skin cancer. Activation of this pathway causes these symptoms, especially after repeated sun exposure, through inflammation-related changes in the skin, such as increased inflammatory cell infiltration, increased oxygen free radicals, increased nitric oxide, and increased matrix metalloproteases, as well as through vascular changes, such as vasodilation and increased vascular permeability. Given this causal relationship between the activation of the kallikrein-kinin pathway and symptoms of photoaging and skin cancer, an inhibitor of the kallikrein-kinin pathway provides effective therapy to treat or prevent symptoms of photoaging or skin cancer.

Inhibiting the Kallikrein-kinin Pathway: Treatment for Photoaging or Skin Cancer The present invention provides a method of treating or preventing photoaging or skin cancer in a patient by administering a compound that inhibits the kallikrein-kinin pathway in the skin. In this regard, an inhibitor of the kallikrein-kinin pathway includes those agents that reduce the effect of a component of the pathway, for example, a tissue kallikrein, plasma kallikrein, a bradykinin, or an enzyme involved in arachidonic acid metabolism (for example, a nonsteroidal anti-inflammatory drug (NSAID)) by inhibiting or antagonizing the enzymatic activity of the component or by reducing the protein level of the component. This inhibition results in a reduction of the inflammation, vasodilation, or vascular permeability, or other kallikrein-kinin pathway-related changes in the skin, that normally occur with activation of the kallikrein-kinin pathway in the skin.

Ideally, a kallikrein inhibitor that is used for treatment is a tissue kallikrein inhibitor. Inhibition of a tissue kallikrein is predicted to be particularly effective in the treatment or prevention of sun-induced photoaging and skin cancer, given their increased release following thermal stimulation and their colocalization with the bradykinin precursor, kininogen (see, e.g., Regoli et al., Pharmacological Reviews 32: 1980; Bhoola et al., Pharmacological Reviews 44: 1992). If a bradykinin inhibitor is used, it is preferably administered topically. Given that bradykinin is an autocoid that acts only locally, topical administration may be used to achieve a therapeutic dose in the skin to inhibit the pathological action of bradykinin without increasing the systemic concentration to a level that would cause adverse systemic side effects.

The treatment contemplates the use of one, or more than one, inhibitor. If multiple inhibitors are used, they can be directed against one or more pathway component. This inhibition of multiple components of the kallikrein-kinin pathway has the advantage of producing an additive or potentiated therapeutic effect and can include a treatment using both a kallikrein inhibitor and a bradykinin inhibitor. The inhibitory effect of a compound can be assessed, for example, by measuring the activity or level of a component of the kallikrein-kinin pathway in the skin, by assessing the appearance or degree of a symptom of photoaging or skin cancer, or by measuring a kallikrein-kinin pathway-related change in the skin, for example, inflammation, inflammatory cell infiltration, oxygen free radicals, nitric oxide, inflammatory cells, MMPs, vasodilation, or vascular permeability.

Ideally, the inhibitor does not completely inhibit the kallikrein-kinin pathway, but, rather, partially inhibits the pathway to reduce or eliminate the effects of sun-induced activation, without affecting other kallikrein-kinin pathway effects that occur in non-exposed skin or in other tissues. Such a result can be achieved through studies of dose response. For example, a series of doses of a kallikrein inhibitor, a bradykinin inhibitor, or an NSAID, can be administered to determine which dose most effectively inhibits the sun-induced effect, without causing significant undesirable side effects.

Techniques to Assess the Effectiveness of a Kallikrein-kinin Pathway Inhibitor

A compound that is known to inhibit a component of the kallikrein-kinin pathway, for example, a known inhibitor of kallikrein or bradykinin activity, or a nonsteroidal anti-inflammatory drug (NSAID), can be assessed for its ability to treat or prevent symptoms of photoaging or skin cancer by testing whether the compound exerts a physiologically relevant effect in biological assays. A compound can be administered before or during exposure, to assess whether it can prevent a kallikrein-kinin pathway mediated effect, or it can be administered after exposure, to determine whether it can reverse the effect. In the case where sun exposure, or UV exposure, produces a kallikrein-kinin related change in the skin, a compound that is an effective inhibitor is one that changes this value back towards the value observed in nonexposed skin in a statistically significant manner. Examples of such assays are provided below.

UV Irradiation of Skin and Preparation of Tissue Samples

To study a compound's efficacy for treating photoaging or skin cancer, assays can be performed on skin samples following irradiation of the skin that produces effects in the skin similar to typical sun exposure. To irradiate skin, for example, fluorescent ultraviolet lights (F36T12 ERE-VHO) are used with a Kodacel filter (TA401/407) to remove ultraviolet light wavelengths of less than 290 nm. The intensity of irradiation is monitored with a phototherapy radiometer and photodetector (International Light, Newburyport, Mass). Total irradiation (290 to 800 nm) at 17 inches from the light source ranges from 0.2 to $20 \times 10^{-3}$ W per square centimeter, preferably, about $1.5 \times 10^{-3}$. The preferred minimal dose to be used is the lowest dose which causes minimally detected erythema 24 hours after exposure. An irradiating dose can be applied for a duration ranging from approximately 15 minutes to 24 hours, or even longer if desired. The dose can also be applied intermittently.

Irradiated and nonirradiated skin samples are taken by keratome or punch biopsy after irradiation, for example, 1–24 hours following radiation. The compound can be applied before, during, or after exposure (Fisher et al., J. Invest. Dermatol. 96: 699–707, 1991; Fisher et al., Nature 379: 335–339, 1996; and Fisher et al., N. Engl. J. Med 337: 1419–1428, 1997).

The effects of UV radiation can be assessed on human subjects or an animal model, such as the hairless, or nude mouse (Mitchell et al., Cancer Res. 59: 2875–84, 1999).

Inhibiting a Component of the Kallikrein-kinin Pathway

The effectiveness of a kallikrein inhibitor, a bradykinin inhibitor, or an NSAID, as treatment for photoaging or skin cancer can be assessed by measuring whether the compound significantly inhibits, respectively, kallikrein activity, bradykinin activity, or the formation of arachidonic acid products such as prostaglandins, leukotrienes, or thromboxanes, in irradiated skin. This reduced activity may result from inhibiting or antagonizing the specific activity of an enzyme or autocoid, or from reducing their protein levels in the skin.

To assay for kallikrein activity, the cleavage of kininogen into bradykinin can be measured, for example, at pH 7.7 and 37 C (Hypertension 7: 172–175, 1985; U.S. Pat. No. 5,464,820).

The effect of bradykinin inhibitors are tested on isolated skin samples according to well accepted methods for bradykinin and related kinins (Trautschold, Handbook of Expt. Pharmacol. Vol. 25, Springer-Verlag, 52–81, 1970; U.S. Pat. Nos. 4,801,613; 5,578,601).

The inhibitory effect of NSAIDs can be assessed by measuring the levels of arachidonic acid products (Trautschold, supra; Vane, Nature New Biol. 231: 232–235, 1971; Vane, Inhibitors of prostaglandins, prostacyclin, and thromboxane synthesis. In Advances in Prostaglandin and Thromboxane Research, vol. 4, ed. Coceanu and Olley, Raven Press, New York, 27–44, 1978).

Measures of Mutagenesis Associated With Skin Cancer

A kallikrein inhibitor, a bradykinin inhibitor, or NSAID that can be used for the present invention, to treat or prevent skin cancer, is one that significantly reduces the mutagenic effects that typically occur with UV exposure. Such effects include the accumulation of damaged DNA in the dermis and epidermis, including the accumulation of pyrimidine dimers. Such damage can be measured, for example, using radioimmunoassay and immunofluorescence micrography (Mitchell et al., Cancer Res. 59: 2875–84, 1999).

Measures of Type I and Type III Collagen

Dermal damage induced by ultraviolet irradiation is principally manifested histologically as a disorganization of collagen fibrils (Bernstein et al., J. Am. Acad. Dermatol. 34: 209–218, 1996) and the accumulation of elastin-containing material (Lavker, Cutaneous aging: chronologic versus photoaging. In: Gilchrist BA ed., Photoaging. Blackwell Science, Cambridge, Mass., 1995, pages 123–125). These changes are manifested biochemically as reduced levels of types I and III collagen precursors and crosslinks, an increased ratio of type III to type I collagen, and an increased level of elastin (Yamauchi et al., J. Invest. Dermatol. 105: 285–290, 1991; Schwartz et al., Photochem. Photobiol. 58: 841–844, 1993; Talwar et al., J. Invest. Dermatol. 34: 209–218, 1995). The effective treatment of photoaged skin is associated with a restoration of procollagen levels to levels observed in unexposed skin (Griffiths et al., N. Engl. J. Med. 329: 530–535, 1993).

To determine whether a kallikrein-kinin pathway inhibitor is efficacious at treating or preventing a symptom of photoaging, irradiated skin samples can be assessed to determine if the presence of the compound significantly changes the skin's collagen composition towards the ratio observed in nonirradiated samples.

To measure type I procollagen cross-linked polypeptide, skin samples are homogenized in 150 mM sodium chloride, 50 mM Tris (pH 7.5), 0.02 percent sodium azide, 2 mM PMSF, and 10 µg/ml aprotinin, and centrifuged at 25,000xg for 30 minutes. Soluble type I collagen is measured by radio assay, for example, using a commercial kit (Incstar, Stillwater, MN; Risteli et al., Clin. Chem. 39: 635–640, 1993).

Assay for Matrix Metalloprotease (MMP) Induction

Irradiation, or sun exposure, to the skin causes an induction of MMPs in the skin. To assess the effectiveness of a kallikrein-kinin pathway inhibitor, collagenase, 92K gelatinase, or stromelysin levels are studied to determine whether the compound reduces the MRNA, protein expression, or total enzymatic activity of these MMPs.

To measure mRNA levels, irradiated skin samples are snap-frozen, and total RNA is isolated and analyzed for collagenase, 92K gelatinase, or stromelysin by northern blot using appropriate probes (Sato et al., Oncogene 8: 395–005, 1987; Fisher et al., J. Invest. Dermat. 96: 699–707, 1991; Angel and Karin, Matrix Suppl. 1: 156–164, 1992; Quinoncs et al., Biochem J. 302, 471–477, 1994; and Fisher et al., J. Invest. Dermatol. 105: 80–86, 1995). Frozen skin sections (5 micron) are mounted, fixed, treated, and hybridized as described in Fisher et al., J. Invest. Dermatol. 105: 80–86, 1995.

To assay for levels of protein in the irradiated skin, supernatant from skin samples homogenized, for example, in 20 mM Tris-HCl, pH 7.6, 5 mM CaCl12, and centrifuged at 3,000xg for 10 min, can be subjected to PAGE-SDS electrophoresis, and protein levels are assessed by western blot. Immunologic analysis of collagenase, gelatinase, and stromelysin is performed, for example, as described in Griffiths et al., N. Engl. J. Med. 329: 530–535, 1993.

Activity levels can be assessed by measuring, for example, hydrolysis of tritium-labeled fibrillar collagen (Hu et al., Analyt. Biochem. 88: 638–643, 1978), or gelatin zymography (Hibbs et al., J. Biol. Chem. 260: 2493–2500, 1985).

Clinical Studies

In addition to, or as a supplement to, the above assays, a compound that is a known inhibitor of a kallikrein or a bradykinin, or a known NSAID, can be assessed for efficacy by administering the compound, systemically or topically, to a patient, and measuring the effect of the compound in reducing or preventing a symptom of photoaging or skin cancer, or a kallikrein-kinin pathway-related change in the skin.

Compounds

Compounds that can be used for the treatment or prevention of photoaging inhibit a kallikrein, a bradykinin, or the arachidonic acid metabolic pathway. Kallikrein or bradykinin inhibitors may act by directly inhibiting or antagonizing the kallikrein or bradykinin pharmacological effect, by reducing the production or release of the kallikrein or bradykinin, or by enhancing the activity of endogenous peptides that degrade kallikrein or bradykinin. Inhibitors of the arachidonic acid metabolic pathway, such as NSAIDs, may act by inhibiting the enzymatic activity of an enzyme in the pathway, for example, cyclooxygenase, prostaglandin synthetase, or lipoxygenase, or by reducing the level of the enzyme in the skin. Examples of such compounds are included below.

Kallikrein Inhibitors

Kallikrein inhibitors that can be used in the treatment or prevention of photoaging inhibit or antagonize the kallikrein enzymatic activity or reduce the kallikrein level in the skin. Kallikrein inhibitors include serpin, C1 inhibitor, α2 macroglobulin, antithrombin-III, ecotin, broad spectrum Kunitz-type serine protease inhibitors (such as aprotinin, and its variants) (U.S. Pat. No. 5,786,328; U.S. Pat. No. 5,770,568), diisopropylfluorophosphate, and pefablock (Interchim).

A key issue in the preferred choice of a kallikrein inhibitor is specificity. The serine protease progenitor of kallikrein also gives rise to other serine proteases, and kallikrein shares many enzymatic features with other proteases. Examples of preferred kallikrein inhibitors that are specific for tissue kallikrein include substrate analog inhibitors of kallikrein, which correspond to the amino acid sequence of kininogen. These peptides have an amino acid sequence comprising positions 388 to 390 of kininogen and prevent the kallikrein cleavage of kininogen (U.S. Pat. No. 5,464,820).

Kallikrein antibodies can also be used.

Bradykinin Inhibitors

The bradykinin inhibitors that can be used to practice the present invention inhibit or antagonize the bradykinin autocoid activity or reduce the bradykinin level in the skin. The inhibitors include icatibant, CP0597, and the exemplary inhibitors listed in U.S. Pat. Nos. 5,700,779; 5,750,506; 5,610,140; 5,863,899, 5,849,863; 5,843,900; 5,834,431, 5,635,593; 5,416,191; 5,620,958; 5,563,162; 5,750,669; 5,574,042; WO 96/13485; WO 96/40639; WO 97/07115; WO 97/11069; EP 773,932 A1; EP 596,406 A1; EP 596,406 B1; EP 787,131 A1; EP 861,243 A1; EP 807,105 A1; EP 622,361 A1; U.S. Pat. No. 5,849,312; U.S. Pat. No. 5,212,182; EP 578,521; EP 564,972; EP 548,825; EP 552,106; FR 2,686,343; and WO 93/11789. The preferred bradykinin inhibitors are specific for the BK2 receptor, such as icatibant and CP0597.

Other bradykinin inhibitors that can be used include the modified peptide analogs disclosed in U.S. Pat. No. 4,801, 613, the nonpeptide antagonists disclosed in U.S. Pat. No. 5,578,601, and the peptide antagonists disclosed in U.S. Pat. No. 4,693,993.

Indirect bradykinin inhibitors which can be used inhibit one or more of the biological activities of bradykinin, and include antihistamines, bradykinin antibodies, benzodiazepine derivatives, high molecular weight ethylene oxide polymers, gallic acid esters, and serotonin inhibitors (U.S. Pat. No. 4,801,613).

Arachidonic Acid Metabolic Pathway Inhibitors

Any known compound that acts as a nonsteroidal anti-inflammatory drug (NSAID) including, but not limited to, salicylates and cyclooxygenase inhibitors can be used. Examples of some well established NSAIDs include naproxen, nabumetone, diclofenac, sulindac, oxaprosin, diflunisal, bromfenac, aspirin, piroxicam, indomethacin, etodolac, ibuprofen, fenoprofen, flurbiprofen, ketorolac, nimesulide, NS-398, and ketoprofen. Salicylates include aspirin, trisalicylates, acetominophen, oxaprosin, and salsalate. Examples of more modern NSAIDs are the cyclooxygenase inhibitors rofecoxib and celecoxib. The above chemicals are commercially available from the following sources: Cayman Chemical Co., Ann Arbor, Mich.; Sigma Chemical Co., St. Louis, Mo.; Proctor and Gamble, Cincinnati, Ohio; G.D. Searle Pharmaceuticals, Chicago, Ill.; and 3M Pharmaceuticals, St. Paul, Minn.

Formulations and Routes of Administration

Compounds can be administered systemically or topically, in an amount sufficient to prevent or treat symptoms of photoaging or skin cancer and may be administered by any appropriate route. For example, systemic administration may be parenteral, intravenous, intra-arterial, subcutaneous, intramuscular, intraperitoneal, intranasal, by aerosol, suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

For topical administration, the compounds will normally be formulated as creams, gels, ointments, sprays, or lotions. Conventional pharmacologically and cosmetically acceptable vehicles may be used. The compounds may also be administered in liposomal formulations that allow compounds to enter the skin. Such liposomal formulations are described, for example, in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and WO 96;40061. Examples of other appropriate vehicles are described in U.S. Pat. No. 4,877,805 and EPA Pub. No. 0586106A1.

The topical formulations may also contain additives such as emollients, skin permeation enhancers, pigments, and perfumes. In addition, the formulation may contain ingredients such as absorbent particles (e.g., polymer beads) that provide sustained release of the inhibitors to the skin. The weight concentration of inhibitor(s) in the formulation will usually be 0.01% to 10%, more usually 0.1% to 1%. Normally, about 50 mg of formulation will be applied per $cm^2$ of skin.

The inhibitors, whether topically or systemically administered, are preferably applied to the skin prior to exposure to sunlight, or prior to the occurrence of any other condition known to exacerbate symptoms of photoaging or skin cancer. The application regimen (i.e., daily, weekly, etc.) will primarily depend upon the longevity (e.g. metabolism, half-life in the skin) of the inhibitor(s) and the molecular targets of their action. It may also be affected by bathing, perspiration, and the extent of sunlight exposure. Usually, the formulation will be applied daily.

As indicated above, one or more inhibitors may be present in a given formulation. Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound will vary depending upon a number of factors, including the dosage of the drug to be administered, and the route of administration.

The formulations can be administered to human patients in therapeutically effective amounts (e.g., amounts which prevent, eliminate, or reduce the symptoms of photoaging or skin cancer) to provide therapy for the disorders described above. The preferred dosage of drug to be administered is likely to depend on such variables as the overall health status of the particular patient, the formulation of the compound excipients, and its route of administration.

Other Embodiments

All publications and patent applications mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art. Other embodiments are within the claims.

What is claimed is:

1. A method of treating or preventing photoaging of the skin, said method comprising administering to a patient a compound that inhibits one or more components of the kallikrein-kinin pathway, in an amount sufficient to reduce or prevent one or more symptoms of photoaging mediated by activation of said pathway.

2. The method of claim 1, wherein said compound reduces or prevents a symptom of photoaging comprising elastosis, atrophy, wrinkling, vascular changes, pigmentary changes, seborrheic keratosis, actinic keratosis, comedones, or cysts.

3. The method of claim 1, wherein said symptom is caused by inflammation, vasodilation, or increased vascular permeability in the skin.

4. The method of claim 1, wherein said compound inhibits kallikrein activity.

5. The method of claim 4, wherein said compound inhibits tissue kallikrein activity.

6. The method of claim 1, wherein said compound inhibits bradykinin activity.

7. The method of claim 6, wherein said compound is selective for inhibiting bradykinin activation of the BK2 receptor.

8. The method of claim 1, wherein said compound is a nonsteroidal anti-inflammatory drug (NSAID).

9. The method of claim 1, wherein said administration is systemic.

10. The method of claim 1, wherein said administration is topical.

11. The method of claim 1, wherein said compound is in a liposomal formulation.

12. A method of claim 1, wherein said compound is administered immediately prior to, or during, photoexposure.

13. A method of assessing whether an inhibitor of the kallikrein-kinin pathway is an effective compound for treating or preventing photoaging, said method comprising contacting said compound with skin before, during, or after photo or UV exposure, and measuring whether said compound significantly reduces a kallikrein-kinin pathway related change in the skin.

14. A method of treating or preventing skin cancer, said method comprising administering to a patient a compound that inhibits one or more components of the kallikrein-kinin pathway, in an amount sufficient to reduce or prevent one or more symptoms of skin cancer mediated by activation of said pathway.

15. The method of claim 14, wherein said compound inhibits a symptom of skin cancer comprising precancerous or cancerous changes to skin morphology, actinic keratosis, basal cell carcinomas, squamous cell carcinomas, or malignant melanoma.

16. The method of claim 14, wherein said symptom is caused by inflammation, vasodilation, or increased vascular permeability in the skin.

17. The method of claim 14, wherein said compound inhibits kallikrein activity.

18. The method of claim 14, wherein said compound inhibits tissue kallikrein activity.

19. The method of claim 14, wherein said compound inhibits bradykinin activity.

20. The method of claim 14, wherein said compound is selective for inhibiting bradykinin activation of the BK2 receptor.

21. The method of claim 14, wherein said compound is a nonsteroidal anti-inflammatory drug (NSAID).

22. The method of claim 14, wherein said administration is systemic.

23. The method of claim 14, wherein said administration is topical.

24. The method of claim 14, wherein said compound is in a liposomal formulation.

25. A method of claim 14, wherein said compound is administered immediately prior to, or during, photoexposure.

26. A method of assessing whether an inhibitor of the kallikrein-kinin pathway is an effective compound for treating or preventing skin cancer, said method comprising contacting said compound with skin before, during, or after photo or UV exposure, and measuring whether said compound significantly reduces a kallikrein-kinin pathway related change in the skin comprising increased oxygen free radicals or increased DNA mutagenesis.

* * * * *